US008221566B1

(12) United States Patent
Chapman

(10) Patent No.: US 8,221,566 B1
(45) **Date of Patent: *Jul. 17, 2012**

(54) PROCESS FOR EMPLOYING HNFX AS A BIOCIDAL EXPLOSIVE

(75) Inventor: Robert D. Chapman, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 347 days.

This patent is subject to a terminal disclaimer.

(21) Appl. No.: 12/615,918

(22) Filed: Nov. 10, 2009

Related U.S. Application Data

(63) Continuation-in-part of application No. 12/496,962, filed on Jul. 2, 2009, now Pat. No. 8,008,527.

(51) Int. Cl.
*D03D 23/00* (2006.01)
*D03D 43/00* (2006.01)

(52) U.S. Cl. .................................................... 149/109.6

(58) Field of Classification Search .................. 588/299; 149/109.6
See application file for complete search history.

(56) References Cited

U.S. PATENT DOCUMENTS

| | | | | |
|---|---|---|---|---|
| 5,693,252 | A * | 12/1997 | Pitochelli | 252/187.21 |
| 6,780,209 | B1 * | 8/2004 | Filippini et al. | 44/347 |
| 7,568,432 | B1 * | 8/2009 | Baker et al. | 102/364 |
| 8,008,527 | B1 * | 8/2011 | Chapman et al. | 564/121 |
| 2008/0190525 | A1 * | 8/2008 | Wagaman | 149/45 |

* cited by examiner

*Primary Examiner* — James McDonough
(74) *Attorney, Agent, or Firm* — Charlene A. Haley

(57) ABSTRACT

A process of making detonation products having an effect on biological agents, providing an effective amount of HNFX; combining HNFX with an additive; detonating the combination with a detonation device; creating detonation products from the combination; contacting the detonation products with the harmful agents; exposing the detonation products for about at least 2 seconds to harmful agents; and destroying the harmful agents.

16 Claims, 1 Drawing Sheet

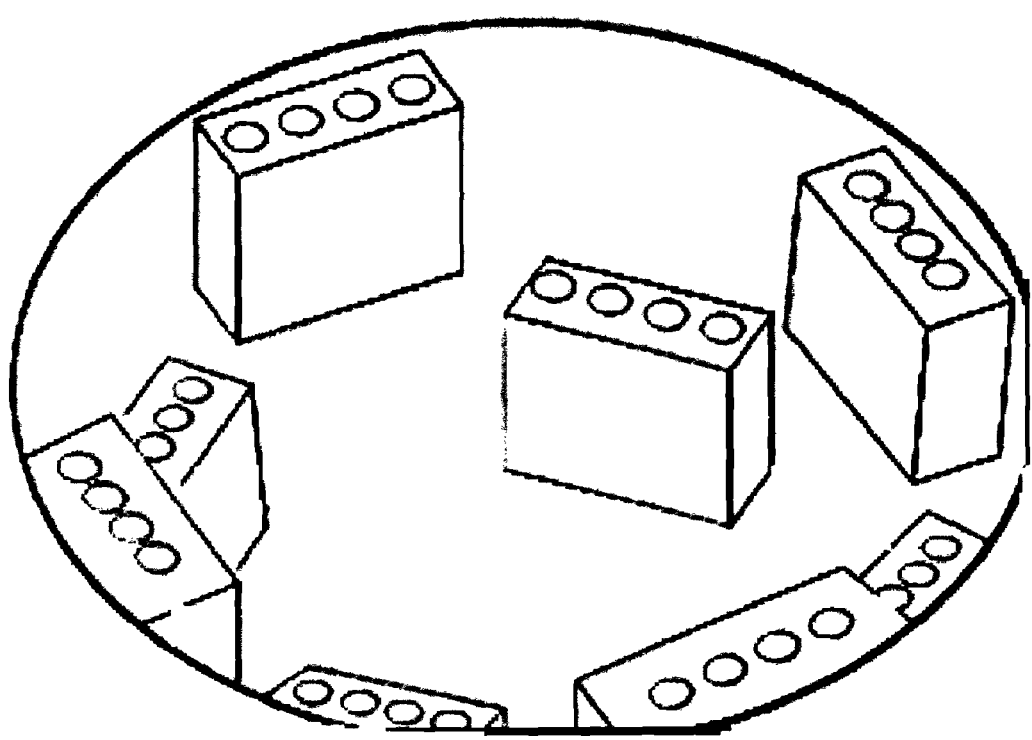

PROCESS FOR EMPLOYING HNFX AS A BIOCIDAL EXPLOSIVE

CROSS-REFERENCE TO RELATED APPLICATIONS

This is a continuation in part application, claiming the benefit of, parent application Ser. No. 12/496,962 filed on Jul. 2, 2009 now U.S. Pat. No. 8,008,527, whereby entire disclosures of application which is hereby incorporated by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

Embodiments of the invention relate to biocidal explosive compositions, methods for producing the same, and methods for eradicating harmful chemical and biological agents, more specifically, HNFX-based explosives that during and/or after detonation produce detonation products that act as efficient biocides upon their exposure.

BACKGROUND OF THE INVENTION

The term "biocide" or "biocidal" refers to a chemical substance capable of killing living organisms, usually in a selective way. Biocides are commonly used in medicine, agriculture, forestry, and in industry where they prevent the fouling of water and oil pipelines. Some substances used as biocides are also employed as anti-fouling agents or disinfectants under other circumstances. The term "biological agent" refers to any living organisms or the materials derived from them (including, but not limited to, bacteria, viruses, fungi, and toxins) that cause disease in or harm to humans that could be used in biological warfare. Harmful biological agents include anthrax (*Bacillus anthracis*) spores. The term "agent" refers to biological agents.

Past agent defeat projects have used hydrogen chloride as a chemical neutralizer, e.g., Lockheed Martin's "Agent Defeat Warhead Device": "These propellants produce gas-phase water and hydrogen chloride that combine to form very reactive hot hydrochloric acid; and as the reactants cool the cooled hydrochloric acid remains in the bunker and may act to continue neutralization of bunker contents for many days . . . . Thus, incendiary agents based on standard composite rocket propellant technology are logical choices for the application described herein." [Jones, J. W. U.S. Pat. No. 6,382,105 (2002)]. It has long been known that HCl has among the poorest bactericidal activities of common acid species. [Paul, T. et al. *Biochemische Zeitschrift* 1911, 29, 202].

Other agent defeat concepts have employed elemental chlorine (a more efficient biocide than HCl) [http://www.globalsecurity.org/military/systems/munitions/adw.htm]. Such formulations so far have produced only low levels of $Cl_2$. One drawback of $Cl_2$ deployment is residual toxic chloro-organics such as chloramines, etc.

In contrast to HCl, hydrogen fluoride (HF) is an efficient antibacterial, antimicrobial biocide: 200 ppm aq. HF destroys *Pseudomonas aeruginosa* and *Saccharomyces diastaticus* in 5 min [Bessems, E.; Junger, R. GB Patent 1584845 (1981)]; and 1-100 ppm aq. HF sterilizes water lines [Tatsuno, T. et al. U.S. Pat. No. 5,147,605 (1992)].

Novel energetic materials have been sought whose deployment would produce biocidal reaction products following explosive events that destroy a structure or containers involving harmful chemical or biological agents, thus neutralizing the agents post-blast. Based on the attractiveness of hydrogen fluoride as a superior agent defeat by-product—from its known biocidal activity—a class of energetic ingredient that appeared particularly promising for incorporation into explosive formulations for the specific application of agent defeat weapons was the class of energetic difluoramines.

Energetic materials have been sought whose deployment would produce biocidal reaction products following explosive events that destroy a structure or containers involving harmful biological agents, thus neutralizing the agents post-blast. Thus, there exists a need in the art for such an explosive that is has high biocidal activity during and/or after detonation, and is an easily synthesized, powerful and efficient chemical neutralizer.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

BRIEF DESCRIPTION OF THE DRAWING

FIG. 1 is a perspective view illustrating a detonation testing device, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

Embodiments of the invention relate to a process of making detonation products having an effect on biological agents including, providing an effective amount of HNFX, detonating the HNFX with a detonation device, creating detonation products from the HFNX, contacting the detonation products with the biological agents, exposing the detonation products for about at least 2 seconds to biological agents, and destroying the biological agents. Another aspect of the invention relates to further including the step of combining the HNFX with an additive. For example, in one embodiment, a 97% HNFX was an effective amount used with a 3% additive which is at least one desensitiser, however, HNFX can be used alone to be successful in producing products to destroy biological agents.

The time of exposure may vary depending on the agents or surrogates of agents that are to be destroyed. For example, in one embodiment, the exposure of the detonation products to the biological agents is for about at least 15 minutes. In another embodiment, the exposure of the detonation products to the biological agents is for about at least 20 minutes. Some detonation products produced by the detonation of HNFX, include, but are not limited to, atomic fluorine and/or hydrogen fluoride. In these processes, the detonation products are also within the scope of the invention.

There are many biological agents that are within the scope of this patent that one skill in the art could use. For example, some biological agents destroyed by the detonation products include, but are not limited to, at least one of *Bacillus anthracis*, *Bacillus subtilis*, and *Bacillus thuringiensis*. For example, other biological agents destroyed by the detonation products include, but are not limited to, *Vibrio cholera* (cholera), *Yersinia pestis* (plague), *Franciscella tularensis* (tularemia, rabbit fever, or deer-fly fever), and *Brucellosis suis* (brucellosis or undulant fever).

Another aspect of the invention relates to a method of producing a biocide, comprising: detonating an N,N-dihaloamine explosive compound to produce a biocidal fluorine derivative, such as atomic fluorine and/or hydrogen fluoride. In these embodiments, the N,N-dihaloamine explosive compound includes at least HNFX.

Harmful biological agents include anthrax (*Bacillus anthracis*) spores. Based on the attractiveness of hydrogen fluoride as a superior agent defeat by-product—from its known biocidal activity—a class of energetic ingredient that appeared particularly promising for incorporation into explosive formulations for the specific application of agent defeat weapons is the class of energetic difluoramines. One such attractive new difluoramine derivative is 3,3,7,7-tetrakis(difluoramino)octahydro-1,5-dinitro-1,5-diazocine (HNFX), which would produce over 39% by weight of biocidal hydrogen fluoride in its detonation products.

HNFX

Experimental Results

FIG. 1 illustrates (left) Detonation chamber used for detonation where *Bacillus* spore samples were placed for testing. Quadruplicate samples of two different *Bacillus* spores (*B. subtilis* and *B. thuringiensis*) at two different location levels (positions 1 and 2) were tested during each detonation. HNFX explosive charge (2.7±0.2 grams) contained in 4-cm$^3$ conductive polypropylene vial, with an RP-3 miniature exploding bridgewire detonator. Denting above the explosive charge at the initiation wire port, was caused by impact of the charge-containing vial.

A stainless steel detonation chamber (8.5 liters in volume) was modified with hardware (Figure) to accommodate biological samples to test the feasibility of novel explosives as effective agent defeat weapon components, specifically to support and protect the samples from direct blast effects while allowing exposure to generated biocidal products of explosion. Three separate detonations of HNFX were carried out in the chamber in order to allow three different exposure times of the analytes to biocidal products of detonation of HNFX, which particularly include hydrogen fluoride. Biological analytes were simulants of anthrax (*Bacillus anthracis*) spores. Spores of *Bacillus subtilis* strain ATCC 6633 and *Bacillus thuringiensis kurstaki* (BGSC 4D1) were used as test organisms. *Bacillus* spores were aliquoted into polypropylene microcentrifuge tubes and allowed to air dry overnight. Microcentrifuge tubes were chosen as containers for the spores in order to support them behind metal shields built into the chamber, which protect them from the direct blast of the explosive charges. Quadruplicate tubes of each *Bacillus* species spore were placed at two different levels in the explosion chamber. Tubes containing dehydrated spores but not placed in the explosion chamber were used as controls.

HNFX explosive charges were 2.7±0.2 grams of pure HNFX with 3% FC-43 Fluorinert™ Electronic Liquid (3M Co.) additive—to reduce electrostatic sensitivity—contained in black conductive polypropylene vials with a volume of 4 cm$^3$. The charge was initiated by an RP-3 miniature exploding bridgewire detonator (Teledyne RISI). Detonation product exposure times were chosen to be 0.4 hour, 2.9 hours, and 24.0 hours. Between each detonation, the chamber was cleaned by wiping first with acetone, followed by an aqueous anionic detergent and a nonionic detergent, and then sterilized with 2% bleach solution. The chamber was finally rinsed with distilled water and with 91% isopropanol. Spore survivability assessments were carried out at the facilities of Sun BioMedical Technologies (Ridgecrest, Calif.).

Spore survivability after detonation was determined by measuring the number of viable spores in both detonation-exposed tubes and control tubes. Spores from each tube were extracted and resuspended using sterile dilution buffer (10% ethanol containing 0.05% Tween 20), serially diluted with buffer and plated onto Nutrient Broth agar plates. Agar plates were incubated at 37° C. for 24 h, and the numbers of colony forming units (CFU) were determined using Quantity One software (Bio-Rad Laboratories). For filter paper swabs, 3 mL of dilution buffer was added to swabs and agitated for 1 min using a vortex shaker. Aliquots of suspension were both plated onto Nutrient Broth agar plates and grown in liquid culture. For confirmation, all extracted spore suspensions were incubated in liquid cultures using Luria-Bertani broth with constant agitation at 37° C. for 24 h. Results: No bacterial colonies grew on Nutrient Broth agar plates for any detonation-exposed samples, even when the incubation time was extended for 48 h. Neither was any bacterial growth observed after 24 h in liquid Luria-Bertani culture at 37° C. The total absence of any viable spores following detonation exposure indicated that no *Bacillus* spores survived exposures to detonation product gases.

Results from spore assays indicated that neither *B. subtilis* nor *B. thuringiensis* spores survived conditions in the explosion chamber. No viable spores were recovered. The overall kill rate, accounting for all *Bacillus* spores, was at least 7 orders of magnitude. Therefore, since the spores were protected from direct blast effects and are known to have significant dry heat resistance, the observed total loss of spore viability following detonations in this experiment is assessed to be due to spores' reactions to biocidal gases and products released during the explosion of HNFX.

Agent Survivability Assessment: HNFX:

Three exposure times: 0.4 hour, 2.9 hours, 24.0 hours. Cross-contamination of the two spore types during detonation was checked by wiping the chamber with sterile filter paper and swabs, then cultured for bacterial growth. Spore survivability was analyzed at Sun BioMedical Technologies.
HNFX Results: 24.0 Hours:

| Samples | Organism | Colony forming units (CFU) |
|---|---|---|
| Bs Control | B. subtilis | $(1.13 \pm 0.27) \times 10^6$ |
| Bt Control | B. thuringiensis | $(1.24 \pm 0.19) \times 10^6$ |
| Detonation 3 (24.0 h) | | |
| Location 1 | B. subtilis | 0 |
| Location 2 | B. subtilis | 0 |
| Location 1 | B. thuringiensis | 0 |
| Location 2 | B. thuringiensis | 0 |
| Swabs | — | 0 |

Viability of *Bacillus* spores following detonation. Control spores (Bs Control and Bt Control) were similarly prepared spore samples that were not exposed to detonation. Results shown are from quadruplicate samples. For the control samples. mean±SD are shown.
HNFX Results: 2.9 Hours:

| Samples | Organism | Colony forming units (CFU) |
|---|---|---|
| Bs Control | B. subtilis | $(1.13 \pm 0.27) \times 10^6$ |
| Bt Control | B. thuringiensis | $(1.24 \pm 0.19) \times 10^6$ |
| Detonation 2 (2.9 h) | | |
| Location 1 | B. subtilis | 0 |
| Location 2 | B. subtilis | 0 |
| Location 1 | B. thuringiensis | 0 |
| Location 2 | B. thuringiensis | 0 |
| Swabs | — | 0 |

Viability of *Bacillus* spores following detonation. Control spores (Bs Control and Bt Control) were similarly prepared spore samples that were not exposed to detonation. Results shown are from quadruplicate samples. For the control samples, mean±SD are shown.
HNFX Results: 0.4 Hour:

| Samples | Organism | Colony forming units (CFU) |
|---|---|---|
| Bs Control | B. subtilis | $(1.13 \pm 0.27) \times 10^6$ |
| Bt Control | B. thuringiensis | $(1.24 \pm 0.19) \times 10^6$ |
| Detonation 1 (0.4 h) | | |
| Location 1 | B. subtilis | 0 |
| Location 2 | B. subtilis | 0 |
| Location 1 | B. thuringiensis | 0 |
| Location 2 | B. thuringiensis | 0 |
| Swabs | — | 0 |

Viability of *Bacillus* spores following detonation. Control spores (Bs Control and Bt Control) were similarly prepared spore samples that were not exposed to detonation. Results shown are from quadruplicate samples. For the control samples, mean±SD are shown.
HNFX Conclusions HNFX is shown to perform as a superior explosive compound that acts biocidally upon exposure of its detonation products, such as hydrogen fluoride, to surrogates of anthrax spores.

No *Bacillus* spores were viable following any exposure time. Spores were shielded from direct blast by steel plates. Light microscopy showed that spore materials were intact, but not viable, following detonation. *Bacillus* (anthraces and surrogates) spores have high dry heat resistance (minutes at 250-300° C. for 4 $\log_{10}$ kill rate). Computations estimate temperature equilibration by radiative heat transfer in <1 msec. No evidence of polypropylene melting, so chamber's contents did not exceed 160~165° C. for >1 sec. Total anthrax surrogate spores=$(1.896\pm0.264)\times10^7$. Kill rate was >7 $\log_{10}$ orders of magnitude [$\log(1.896\times10^7)$]. Agent defeat was not due to heat or pressure but harsh conditions of exposure to biocidal detonation products, proposed as HF or atomic fluorine. Unexpected results showed that anthrax surrogate kill rate was higher than expected (namely, complete) after short exposures to HNFX detonation products. As a result, HNFX was demonstrated to be totally effective (>7 orders of magnitude) in destroying surrogates of anthrax spores via its detonation products, being more effective than alternative explosive compositions that have been deployed for harmful agent defeat.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A process of making detonation products having an effect on biological agents, comprising:
    providing an effective amount of HNFX;
    detonating said HNFX with a detonation device;
    creating detonation products from said HNFX;
    contacting the detonation products with the biological agents;
    exposing said detonation products for about at least 2 seconds to biological agents; and
    destroying the biological agents.

2. The process according to claim 1, further comprising combining said HNFX with an additive.

3. The process according to claim 1, wherein said exposing of said detonation products to the biological agents is for about at least 15 minutes.

4. The process according to claim 1, wherein said exposing of said detonation products to the biological agents is for about at least 20 minutes.

5. The process according to claim 1, wherein said detonation products comprises of at least atomic fluorine.

6. The process according to claim 1, wherein said detonation products comprises of at least hydrogen fluoride.

7. The process according to claim 1, wherein said detonation products comprises of at least atomic fluorine and hydrogen fluoride.

8. The process according to claim 1, wherein said detonation products destroy biological agents which comprises of at least one of *Bacillus anthracis*, *Bacillus subtilis*, and *Bacillus thuringiensis*.

9. The process according to claim 1, wherein said detonation products destroy biological agents which comprises of at least one of *Vibrio cholera*, *Yersinia pestis*, *Franciscella tularensis*, and *Brucellosis suis*.

10. The process according to claim 1, wherein said effective amount of HFNX is about 97%.

11. The process according to claim 2, wherein said additive is a desensitiser.

12. The process according to claim 2, where said additive is about 3%.

13. A method of producing a biocide, comprising: detonating an N,N-dihaloamine explosive compound to produce a biocidal atomic fluorine derivative.

14. A method of producing a biocide, comprising: detonating an N,N-dihaloamine explosive compound to produce a biocidal atomic fluorine derivative, wherein said N,N-dihaloamine explosive compound which comprises of at least HNFX.

15. A method of producing a biocide, comprising: detonating a N,N-dihaloamine explosive compound to produce biocidal hydrogen fluoride.

16. A method of producing a biocide, comprising: detonating a N,N-dihaloamine explosive compound to produce biocidal hydrogen fluoride, wherein said N,N-dihaloamine explosive compound which comprises of at least HNFX.

* * * * *